United States Patent

Clough et al.

Patent Number: 5,124,353
Date of Patent: Jun. 23, 1992

[54] FUNGICIDAL ALPHA-SUBSTITUTED ACRYLATES

[75] Inventors: John M. Clough, Marlow; Christopher R. A. Godfrey, Bracknell, both of England

[73] Assignee: Imperial Chemical Industries PLC, London

[21] Appl. No.: 416,609

[22] Filed: Oct. 3, 1989

Related U.S. Application Data

[62] Division of Ser. No. 264,874, Oct. 31, 1988, Pat. No. 4,913,721, which is a division of Ser. No. 893,272, Aug. 5, 1986, Pat. No. 4,802,913.

[30] Foreign Application Priority Data

Aug. 22, 1985 [GB] United Kingdom ............... 8521082

[51] Int. Cl.$^5$ ............... A01N 37/10; C07C 69/612
[52] U.S. Cl. ............... 514/510; 71/76; 71/88; 71/90; 71/92; 71/94; 71/95; 71/98; 71/108; 514/269; 514/532; 544/334; 544/335; 560/10; 560/15; 560/17; 560/56; 560/57; 560/59; 560/60; 560/61; 560/62
[58] Field of Search ............... 560/10, 15, 56, 57, 560/59, 60; 514/510, 532

[56] References Cited

U.S. PATENT DOCUMENTS

| | | | |
|---|---|---|---|
| 3,922,345 | 11/1975 | Lipinski | 424/251 |
| 3,941,889 | 3/1976 | Lipinski | 424/251 |
| 4,104,049 | 8/1978 | Maurer et al. | 561/43 |
| 4,267,355 | 5/1981 | Scott et al. | 560/43 |
| 4,492,683 | 1/1985 | Nagpal | 560/43 |

FOREIGN PATENT DOCUMENTS

0178826 4/1986 European Pat. Off.

OTHER PUBLICATIONS

Tanaka, et al., "Chemical Abstracts", vol. 90, 1979, col. 90:22469y.
Chemical Abstracts 55 17492c (Rec. Trav. Chim. 79 937-49 (1960).
Chemical Abstracts 55 27350c (J. Org. Chem. 26 2770-8 (1961).
Chemical Abstracts 90 22469v (Chem. Pharm. Bull. 26(5) 1558-69 (1978).
Chemical Abstracts 90 71791c (Chem. Ber. 111 (12) 3879-91).
Chemical Abstracts 95 186931u (J. Chem. Res. 1981(7). 18C-1).

*Primary Examiner*—C. Warren Ivy
*Assistant Examiner*—James H. Turnipseed
*Attorney, Agent, or Firm*—Cushman, Darby & Cushman

[57] ABSTRACT

Compounds of formula (I):

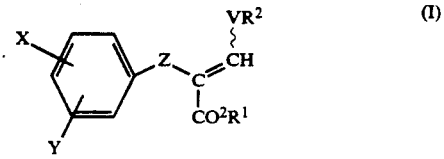

and stereoisomers thereof, wherein V is an oxygen or a sulphur atom; X and Y, which may be the same or different, are hydrogen or halogen atoms, or optionally substituted alkyl, optionally substituted alkenyl, optionally substituted aryl, optionally substituted heteroaryl, optionally substituted alkynyl, haloalkyl, alkoxy, haloalkoxy, optionally substituted aryloxy, optionally substituted arylalkoxy, optionally substituted acyloxy, optionally substituted amino, acylamino, nitro, nitrile, $-CO_2R^3$, $-CONR^4R^5$, or $-COR^6$ groups; or the groups X and Y, when they are in adjacent positions on the phenyl ring, may join to form a fused ring, either aromatic or aliphatic, optionally containing one or more heteroatoms; and Z is optionally substituted methylene, optionally substituted amino, oxygen or sulphur and when Z is a substituted methylene group, the substituent may join the 2-position of the phenyl ring to form a non-aromatic fused ring; $R^1$ and $R^2$ are alkyl groups containing from one to four carbon atoms, optionally substituted with one or more halogen atoms; and $R^3$, $R^4$, $R^5$, and $R^6$, which may be the same or different, are hydrogen atoms or optionally substituted alkyl, cycloalkyl, alkenyl, alkynyl, optionally substituted aryl, optionally substituted aralkyl, or cycloalkylalkyl groups: and metal complexes thereof.

7 Claims, No Drawings

FUNGICIDAL ALPHA-SUBSTITUTED ACRYLATES

This is a division of application Ser. No. 07/264,874, filed Oct. 31, 1988, now issued as U.S. Pat. No. 4,913,721, which is a division of application Ser. No. 06/893,272, filed Aug. 5, 1986, now U.S. Pat. No. 4,802,913.

This invention relates to compounds useful as fungicides, to processes for preparing them, to fungicidal compositions containing them and to methods of combating fungi, especially fungal infections in plants.

The invention provides compounds having the general formula (I):

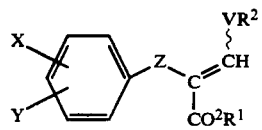

and stereoisomers thereof, wherein V is an oxygen or a sulphur atom; X and Y, which may be the same or different, are hydrogen or halogen atoms, or optionally substituted alkyl, optionally substituted alkenyl, optionally substituted aryl, optionally substituted heteroaryl, optionally substituted alkynyl, haloalkyl, alkoxy, haloalkoxy, optionally substituted aryloxy, optionally substituted arylalkoxy, optionally substituted acyloxy, optionally substituted amino, acylamino, nitro, nitrile, $-CO_2R^3$, $-CONR^4R^5$, or $-COR^6$ groups; or the groups X and Y, when they are in adjacent positions on the phenyl ring, may join to form a fused ring, either aromatic or aliphatic, optionally containing one or more heteroatoms; and Z is optionally substituted methylene, optionally substituted amino, oxygen or sulphur and when Z is a substituted methylene group, the substituent may join the 2-position of the phenyl ring to form a non-aromatic fused ring; $R^1$ and $R^2$ are alkyl groups containing from one to four carbon atoms, optionally substituted with one or more halogen atoms; and $R^3$, $R^4$, $R^5$ and $R^6$, which may be the same or different, are hydrogen atoms or optionally substituted alkyl, cycloalkyl, alkenyl, alkynyl, optionally substituted aryl, optionally substituted aralkyl, or cycloalkylalkyl groups; and metal complexes thereof.

The compounds of the invention contain at least one carbon-carbon double bond, and are sometimes obtained in the form of mixtures of geometric isomers. However, these mixtures can be separated into individual isomers, and this invention embraces such isomers.

The individual isomers which result from the substituted double bond of the acrylate group are hereinafter identified by the commonly used terms "E" and "Z". These terms are defined according to the Cahn-Ingold-Prelog system which is fully described in the literature (see, for example, J March, "Advanced Organic Chemistry" 3rd edition, Wiley-Interscience, Page 109 et seq).

The compounds of this invention include those which are predominantly in the form of the E-isomer and also those which are predominantly in the form of the Z-isomer.

The use hereinafter of the formula:

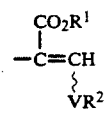

signifies a separable mixture of both geometric isomers about the acrylate double bond, ie.

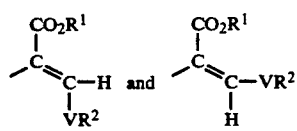

Examples of X and Y when they are aryl groups are optionally substituted phenyl- or optionally substituted naphthyl-groups. Examples of X and Y when they are heteroaryl groups are optionally substituted pyridyl-, optionally substituted pyrimidinyl-, optionally substituted thienyl-, optionally substituted furyl-, or optionally substituted pyrrolyl-groups, each linked via any ring atom (for example, X or Y is a 2-pyridyl, 3-pyridyl-, or 4-pyridyl-group, each optionally substituted).

In preferred compounds, X is an optionally substituted aryl- or an optionally substituted heteroaryl-group in the 3-position of the phenyl ring linked to the atom or group Z, that is, positioned meta to the group Z. In preferred compounds, $R^1$ and $R^2$ are both methyl groups.

Alkyl groups can be in the form of straight or branched chains, and preferably contain 1 to 4 carbon atoms; examples are methyl, ethyl, n-propyl, iso-propyl, n-butyl, sec-butyl, iso-butyl and tert-butyl.

In a further aspect, therefore, the invention provides a compound having the formula (I) above wherein V is oxygen or sulphur; X is H, $C_{1-4}$ alkyl, $C_{3-4}$ alkenyl, halogen, phenyl, naphthyl, pyridyl, pyrimidinyl, benzyl, phenoxy, benzyloxy, pyridyloxy, furyl, thienyl, benzothienyl or pyrrolyl, each optionally substituted with one or more halogen atoms or $C_{1-4}$ alkyl, $C_{1-4}$ alkoxy or halo $C_{1-4}$ alkyl groups; Y is hydrogen or a halogen; and Z is $-CH_2-$, $-CH(CH_3)-$, $-C(CH_3)_2-$, $-O-$, $-S-$, $-N(CH_3)-$, or $-N(C_2H_5)-$; and $R^1$ and $R^2$ are both methyl.

In a still further aspect the invention provides a compound as defined in the preceding paragraphs wherein X is attached to the phenyl ring at the meta- (or 3-) position relative to the group Z, and X is a phenyl, naphthyl, pyridyl, pyrimidinyl, furyl, thienyl, benzothinnyl or pyrrolyl group each linked through any one of their ring atoms and each optionally substituted with one or more halogen atoms or $C_{1-4}$ alkyl, $C_{1-4}$ alkoxy or halo $C_{1-4}$ alkyl groups.

Examples of the compounds of the invention are shown in Tables 1 and 2. In these Tables "Ph" stands for phenyl i.e. $C_6H_5$.

TABLE 1

V = oxygen; $R^1 = R^2 = CH_3$

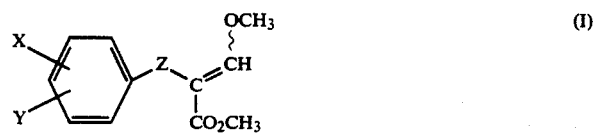

(I)

| Compound No. | X | Y | Z | Melting Point (°C.) | Olefinic* | Isomer+ |
|---|---|---|---|---|---|---|
| 1 | H | H | $CH_2$ | oil | 7.40 | E |
| 2 | H | H | $CH(CH_3)$ | oil | 7.31 | E |
| 3 | H | H | $C(CH_3)_2$ | oil | 7.21 | E |
| 4 | 2-Ph | H | $CH_2$ | oil | under aromatics | E |
| 5 | 3-Ph | H | $CH_2$ | oil | under aromatics | E |
| 6 | 4-Ph | H | $CH_2$ | oil | under aromatics | E |
| 7 | H | H | $C(CH_3)_2$ | oil | 6.34 | Z |
| 8 | H | H | $N(CH_3)$ | oil | 7.38 | Z |
| 9 | 2-Ph | H | $N(CH_3)$ | | | Z |
| 10 | 3-Ph | H | $N(CH_3)$ | oil | 7.38 | Z |
| 11 | 4-Ph | H | $N(CH_3)$ | | | Z |
| 12 | H | H | O | 52–53 | 7.31 | Z |
| 13 | 2-Ph | H | O | 119–120 | 7.30 | Z |
| 14 | 3-Ph | H | O | 111–113 | 7.32 | Z |
| 15 | 4-Ph | H | O | 71–72.5 | 7.34 | Z |
| 16 | 1-naphthyl⊕ | | O | 87–88 | 7.40 | Z |
| 17 | 2-naphthyl⊕ | | O | 116–117 | 7.40 | Z |
| 18 | 3-tert-butyl | H | O | 55.5–56 | 7.32 | Z |
| 19 | 4-tert-butyl | H | O | 70–72 | 7.32 | Z |
| 20 | 3-PhO | H | O | 61.5–62.5 | 7.29 | Z |
| 21 | 4-PhO | H | O | 140–141 | 7.32 | Z |
| 22 | 2-PhCH$_2$O | H | O | 135–136 | 7.29 | Z |
| 23 | CF$_3$-pyridyl-O- | H | O | oil | 7.35 | Z |
| 24 | H | H | S | 61–62.5 | 7.98 | Z |
| 25 | 2-Ph | H | S | | | Z |
| 26 | 3-Ph | H | S | oil | 8.02 | Z |
| 27 | 4-Ph | H | S | | | Z |
| 28 | 3-n-$C_{15}H_{31}$ | H | O | 48.5–49.5 | 7.31 | Z |
| 29 | 3-(2-Cl—$C_6H_4$) | H | $CH_2$ | | | E |
| 30 | 3-(2-Cl—$C_6H_4$) | H | O | | | Z |
| 31 | 3-(2-Cl—$C_6H_4$) | H | S | | | Z |
| 32 | 3-(2-Cl—$C_6H_4$) | H | $N(CH_3)$ | | | Z |
| 33 | 3-(2-Cl—$C_6H_4$) | 6-F | $N(CH_3)$ | | | Z |
| 34 | 3-(3-Cl—$C_6H_4$) | H | $CH_2$ | | | E |
| 35 | 3-(3-Cl—$C_6H_4$) | H | O | | | Z |
| 36 | 3-(3-Cl—$C_6H_4$) | H | S | | | Z |
| 37 | 3-(3-Cl—$C_6H_4$) | H | $N(CH_3)$ | | | Z |
| 38 | 3-(3-Cl—$C_6H_4$) | 5-F | $N(CH_3)$ | | | Z |
| 39 | 3-(4-Cl—$C_6H_4$) | H | $CH_2$ | | | E |
| 40 | 3-(4-Cl—$C_6H_4$) | H | O | | | Z |
| 41 | 3-(4-Cl—$C_6H_4$) | H | S | | | Z |
| 42 | 3-(4-Cl—$C_6H_4$) | H | $N(CH_3)$ | | | Z |
| 43 | 3-(4-Cl—$C_6H_4$) | 4-F | $N(CH_3)$ | | | Z |
| 44 | 3-(2-F—$C_6H_4$) | H | $CH_2$ | | | E |
| 45 | 3-(2-F—$C_6H_4$) | H | O | | | Z |
| 46 | 3-(2-F—$C_6H_4$) | H | S | | | Z |
| 47 | 3-(2-F—$C_6H_4$) | H | $N(CH_3)$ | | | Z |
| 48 | 3-(2-F—$C_6H_4$) | 2-F | $N(CH_3)$ | | | Z |
| 49 | 3-(3-F—$C_6H_4$) | H | $CH_2$ | | | E |
| 50 | 3-(3-F—$C_6H_4$) | H | O | | | Z |
| 51 | 3-(3-F—$C_6H_4$) | H | S | | | Z |
| 52 | 3-(3-F—$C_6H_4$) | H | $N(CH_3)$ | | | Z |
| 53 | 3-(4-F—$C_6H_4$) | H | $CH_2$ | | | E |
| 54 | 3-(4-F—$C_6H_4$) | H | O | | | Z |
| 55 | 3-(4-F—$C_6H_4$) | H | S | | | Z |
| 56 | 3-(4-F—$C_6H_4$) | H | $N(CH_3)$ | | | Z |
| 57 | 3-(2-$CH_3O$—$C_6H_4$) | H | $CH_2$ | | | E |
| 58 | 3-(2-$CH_3O$—$C_6H_4$) | H | O | | | Z |
| 59 | 3-(2-$CH_3O$—$C_6H_4$) | H | S | | | Z |
| 60 | 3-(2-$CH_3O$—$C_6H_4$) | H | $N(CH_3)$ | | | Z |
| 61 | 3-(3-$CH_3O$—$C_6H_4$) | H | $CH_2$ | | | E |
| 62 | 3-(3-$CH_3O$—$C_6H_4$) | H | O | Oil | 7.34 | Z |
| 63 | 3-(3-$CH_3O$—$C_6H_4$) | H | S | | | Z |
| 64 | 3-(3-$CH_3O$—$C_6H_4$) | H | $N(CH_3)$ | | | Z |
| 65 | 3-(4-$CH_3O$—$C_6H_4$) | H | $CH_2$ | | | E |

TABLE 1-continued $V = oxygen; R^1 = R^2 = CH_3$

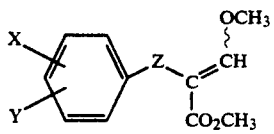

(I)

| Compound No. | X | Y | Z | Melting Point (°C.) | Olefinic* | Isomer+ |
|---|---|---|---|---|---|---|
| 66 | 3-(4-CH$_3$O—C$_6$H$_4$) | H | O | | | Z |
| 67 | 3-(4-CH$_3$O—C$_6$H$_4$) | H | S | | | Z |
| 68 | 3-(4-CH$_3$O—C$_6$H$_4$) | H | N(CH$_3$) | | | Z |
| 69 | 3-(2-CH$_3$—C$_6$H$_4$) | H | CH$_2$ | | | E |
| 70 | 3-(2-CH$_3$—C$_6$H$_4$) | H | O | | | Z |
| 71 | 3-(2-CH$_3$—C$_6$H$_4$) | H | S | | | Z |
| 72 | 3-(2-CH$_3$—C$_6$H$_4$) | H | N(CH$_3$) | | | Z |
| 73 | 3-(3-CH$_3$—C$_6$H$_4$) | H | CH$_2$ | | | E |
| 74 | 3-(3-CH$_3$—C$_6$H$_4$) | H | O | | | Z |
| 75 | 3-(3-CH$_3$—C$_6$H$_4$) | H | S | | | Z |
| 76 | 3-(3-CH$_3$—C$_6$H$_4$) | H | N(CH$_3$) | | | Z |
| 77 | 3-(4-CH$_3$—C$_6$H$_4$) | H | CH$_2$ | | | E |
| 78 | 3-(4-CH$_3$—C$_6$H$_4$) | H | O | | | Z |
| 79 | 3-(4-CH$_3$—C$_6$H$_4$) | H | S | | | Z |
| 80 | 3-(4-CH$_3$—C$_6$H$_4$) | H | N(CH$_3$) | | | Z |
| 81 | 3-(3,4-di-F—C$_6$H$_3$) | H | CH$_2$ | | | E |
| 82 | 3-(3,4-di-F—C$_6$H$_3$) | H | O | | | Z |
| 83 | 3-(3,4-di-F—C$_6$H$_3$) | H | S | | | Z |
| 84 | 3-(3,4-di-F—C$_6$H$_3$) | H | N(CH$_3$) | | | Z |
| 85 | 3-(2,4-di-F—C$_6$H$_3$) | H | CH$_2$ | | | E |
| 86 | 3-(2,4-di-F—C$_6$H$_3$) | H | O | | | Z |
| 87 | 3-(2,4-di-F—C$_6$H$_3$) | H | S | | | Z |
| 88 | 3-(2,4-di-F—C$_6$H$_3$) | H | N(CH$_3$) | | | Z |
| 89 | 3-(3-Cl,4-F—C$_6$H$_3$) | H | CH$_2$ | | | E |
| 90 | 3-(3-Cl,4-F—C$_6$H$_3$) | H | O | | | Z |
| 91 | 3-(3-Cl,4-F—C$_6$H$_3$) | H | S | | | Z |
| 92 | 3-(3-Cl,4-F—C$_6$H$_3$) | H | N(CH$_3$) | | | Z |
| 93 | 3-(pyrid-2-yl) | H | CH$_2$ | | | E |
| 94 | 3-(pyrid-2-yl) | H | O | Oil | 7.34 | Z |
| 95 | 3-(pyrid-2-yl) | H | S | | | Z |
| 96 | 3-(pyrid-2-yl) | H | N(CH$_3$) | | | Z |
| 97 | 3-(pyrid-3-yl) | H | CH$_2$ | | | E |
| 98 | 3-(pyrid-3-yl) | H | O | | | Z |
| 99 | 3-(pyrid-3-yl) | H | S | | | Z |
| 100 | 3-(pyrid-3-yl) | H | N(CH$_3$) | | | Z |
| 101 | 3-(pyrid-4-yl) | H | CH$_2$ | | | E |
| 102 | 3-(pyrid-4-yl) | H | O | | | Z |
| 103 | 3-(pyrid-4-yl) | H | S | | | Z |
| 104 | 3-(pyrid-4-yl) | H | N(CH$_3$) | | | Z |
| 105 | 3-(2-thienyl) | H | CH$_2$ | | | E |
| 106 | 3-(2-thienyl) | H | O | | | Z |
| 107 | 3-(2-thienyl) | H | S | | | Z |
| 108 | 3-(2-thienyl) | H | N(CH$_3$) | | | Z |
| 109 | 3-(3-thienyl) | H | CH$_2$ | | | E |
| 110 | 3-(3-thienyl) | H | O | | | Z |
| 111 | 3-(3-thienyl) | H | S | | | Z |
| 112 | 3-(3-thienyl) | H | N(CH$_3$) | | | Z |
| 113 | 3-(2-furyl) | H | CH$_2$ | | | E |
| 114 | 3-(2-furyl) | H | O | | | Z |
| 115 | 3-(2-furyl) | H | S | | | Z |
| 116 | 3-(2-furyl) | H | N(CH$_3$) | | | Z |
| 117 | 3-(3-furyl) | H | CH$_2$ | | | E |
| 118 | 3-(3-furyl) | H | O | | | Z |
| 119 | 3-(3-furyl) | H | S | | | Z |
| 120 | 3-(3-furyl) | H | N(CH$_3$) | | | Z |
| 121 | 3-(3-CH$_3$O-pyrid-2-yl) | H | CH$_2$ | | | E |
| 122 | 3-(3-CH$_3$O-pyrid-2-yl) | H | O | | | Z |
| 123 | 3-(3-CH$_3$O-pyrid-2-yl) | H | S | | | Z |
| 124 | 3-(3-CH$_3$O-pyrid-2-yl) | H | N(CH$_3$) | | | Z |
| 125 | 3-(2-benzothienyl) | H | CH$_2$ | | | E |
| 126 | 3-(2-benzothienyl) | H | O | | | Z |
| 127 | 3-(2-benzothienyl) | H | S | | | Z |
| 128 | 3-(2-benzothienyl) | H | N(CH$_3$) | | | Z |
| 129 | 3-(3-benzothienyl) | H | CH$_2$ | | | E |
| 130 | 3-(3-benzothienyl) | H | O | | | Z |
| 131 | 3-(3-benzothienyl) | H | S | | | Z |
| 132 | 3-(3-benzothienyl) | H | N(CH$_3$) | | | Z |
| 133 | 3-(5-CH$_3$O-pyrid-2-yl) | H | CH$_2$ | | | E |
| 134 | 3-(5-CH$_3$O-pyrid-2-yl) | H | O | | | Z |
| 135 | 3-(5-CH$_3$O-pyrid-2-yl) | H | S | | | Z |
| 136 | 3-(5-CH$_3$O-pyrid-2-yl) | H | N(CH$_3$) | | | Z |

TABLE 1-continued $V = oxygen; R^1 = R^2 = CH_3$

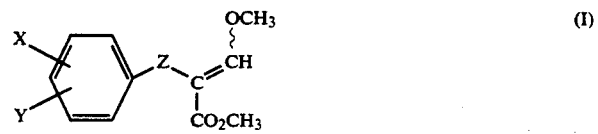

| Compound No. | X | Y | Z | Melting Point (°C.) | Olefinic* | Isomer+ |
|---|---|---|---|---|---|---|
| 137 | (A) | (A) | (A) | oil | 7.44 | E |
| 138 | (B) | (B) | (B) | 124–125.5 | 7.59 | E |
| 139 | 3-(pyrrol-1-yl) | H | $CH_2$ | | | E |
| 140 | 3-(pyrrol-1-yl) | H | O | | | Z |
| 141 | 3-(pyrrol-1-yl) | H | S | | | Z |
| 142 | 3-(pyrrol-1-yl) | H | $N(CH_3)$ | | | Z |
| 143 | 3-Ph | H | $N(CH_2CH_3)$ | | | Z |
| 144 | 3-Cl | H | $N(CH_3)$ | Oil | 7.43 | Z |
| 145 | 3-Cl | 6-Cl | $N(CH_3)$ | | | Z |
| 146 | (C) | H | O | 126–130 | 7.32 | Z |

(A): Compound No. 137 is $C_6H_5$—

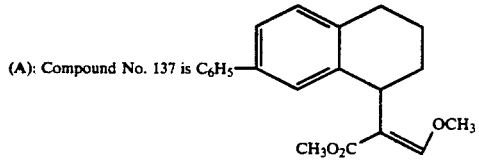

(B): Compound No. 138 is $C_6H_5$—

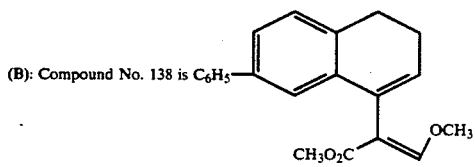

(C): Compound No. 146 is

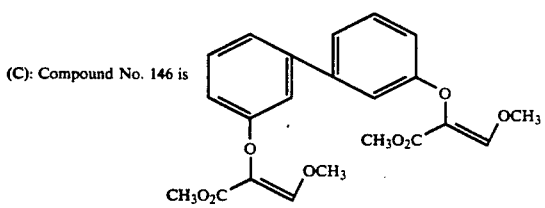

*Chemical shift of singlet from olefinic proton on beta-methoxyacrylate group (ppm from tetramethylsilane). Solvent: $CDCl_3$.
+Geometry of beta-methoxyacrylate group.
⊕Substituents X and Y join to form a fused ring.

TABLE 2

$V = sulphur; R^1 = R^2 = CH_3$

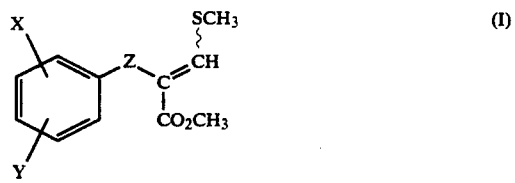

| Compound No | X | Y | Z | Melting Point (°C.) | Olefinic* | Isomer+ |
|---|---|---|---|---|---|---|
| 1 | 3-Ph | H | $CH_2$ | | | E |
| 2 | 3-Ph | H | O | | | Z |
| 3 | 3-Ph | H | S | | | Z |
| 4 | 3-Ph | H | $NCH_3$ | | | Z |
| 5 | 3-(3-Cl—$C_6H_4$) | H | $CH_2$ | | | E |
| 6 | 3-(3-Cl—$C_6H_4$) | H | O | | | Z |
| 7 | 3-(3-Cl—$C_6H_4$) | H | S | | | Z |
| 8 | 3-(3-Cl—$C_6H_4$) | H | $NCH_3$ | | | Z |
| 9 | 3-(pyrid-2-yl) | H | $CH_2$ | | | E |
| 10 | 3-(pyrid-2-yl) | H | O | | | Z |
| 11 | 3-(pyrid-2-yl) | H | S | | | Z |
| 12 | 3-(pyrid-2-yl) | H | $NCH_3$ | | | Z |
| 13 | 3-(3-methoxy-pyrid-2-yl) | H | $CH_2$ | | | E |
| 14 | 3-(3-methoxy-pyrid-2-yl) | H | O | | | Z |

TABLE 2-continued

V = sulphur; $R^1 = R^2 = CH_3$

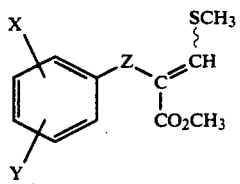

(I)

| Compound No | X | Y | Z | Melting Point (°C.) | Olefinic* | Isomer+ |
|---|---|---|---|---|---|---|
| 15 | 3-(3-methoxy-pyrid-2-yl) | H | S | | | Z |
| 16 | 3-(3-methoxy-pyrid-2-yl) | H | NCH$_3$ | | | Z |

*Chemical shift of singlet from olefinic proton on beta-(methylthio)-acrylate group (ppm from tetramethylsilane). Solvent CDCl$_3$
+Geometry of beta-(methylthio)acrylate group.

TABLE 3

SELECTED PROTON NMR DATA

Table 3 shows selected proton nmr data for certain compounds described in Tables 1 and 2. Only certain absorptions are shown for each compound; no attempt is made to list every absorption. Chemical shifts are measured in ppm from tetramethylsilane, and deuterochloroform was used as solvent throughout. The following abbreviations are used:

| br = broad | t = triplet |
|---|---|
| s = singlet | q = quartet |
| d = doublet | m = multiplet |
| J = coupling constant | Hz = Hertz |

| Table No. | Compound No. | Data |
|---|---|---|
| 1 | 1 | 3.58 (3H, s); 3.65 (3H, s); 3.85 (2H, s); 7.40 (1H, s) |
| 1 | 2 | 1.54 (3H, d, J 9Hz); 3.62 (3H, s); 3.82 (3H, s); 4.21 (1H, q J 9Hz); 7.31 (1H, s) |
| 1 | 3 | 1.62 (6H, s); 3.49 (3H, s); 3.74 (3H, s); 7.21 (1H, s) |
| 1 | 4 | 3.54 (2H, s); 3.59 (3H, s); 3.76 (3H, s); 7.16–7.46 (10H, m) |
| 1 | 5 | 3.61 (2H, s); 3.64 (3H, s); 3.80 (3H, s) |
| 1 | 6 | 3.62 (2H, s); 3.71 (3H, s); 3.90 (3H, s); 7.25–7.60 (10H, m) |
| 1 | 7 | 1.54 (6H, s); 3.54 (3H, s); 3.75 (3H, s); 6.34 (1H, s) |
| 1 | 8 | 3.05 (3H, s); 3.65 (3H, s); 3.84 (3H, s); 6.6–6.75 (3H, m); 7.1–7.25 (2H, m); 7.38 (1H, s) |
| 1 | 10 | 3.10 (3H, s); 3.64 (3H, s); 3.80 (3H, s); 7.38 (1H, s) |
| 1 | 23 | 3.78 (3H, s); 3.92 (3H, s); 6.9–7.1 (5H, m); 7.35 (1H, s); 7.90 (1H, dd, J 9 and 3Hz); 8.50 (1H, br s) |
| 1 | 26 | 2.42 (3H, s); 3.78 (3H, s); 4.00 (3H, s); 8.02 (1H, s) |
| 1 | 62 | 3.72 (3H, s); 3.85 (3H, s); 3.87 (3H, s); 6.8–7.0 (2H, m); 7.0–7.5 (6H, m); 7.34 (1H, s) |
| 1 | 94 | 3.72 (3H, s); 3.87 (3H, s); 6.9–7.1 (1H, m); 7.1–7.9 (6H, m); 7.34 (1H, s); 8.68 (1H, sextet) |
| 1 | 144 | 3.04 (3H, s); 3.69 (3H, s); 3.88 (3H, s); 6.4–6.8 (3H, m); 7.12 (1H, t); 7.43 (1H, s) |
| 1 | 146 | 3.72 (6H, s); 3.87 (6H, s); 6.8–7.0 (2H, m); 7.1–7.5 (6H, m); 7.32 (2H, s) |
| 1 | 137 | 1.65–1.84 (1H, m); 1.85–2.01 (3H, m); 2.72–2.98 (2H, m); 3.58 (3H, s); 3.76 (3H, s); 4.14–4.22 (1H, m); 7.44 (1H, s) |

The compounds of the invention having the general formula (I) can be prepared by the steps shown in Scheme 1. In Scheme 1, the terms X, Y, Z, $R^1$ and $R^2$ are as defined above; $R^3$ is an alkyl group, especially a methyl group; and L is a halogen atom or another good leaving group.

Thus, compounds of general formula (I), which may exist as mixtures of geometric isomers which can be separated by chromatography, fractional crystallisation or distillation, can be prepared by treatment of compounds of general formula (IIa) or (IIb) with an alkylating agent such as $R^2L$ (III) in the presence of an acid-binding agent (such as potassium carbonate) in a suitable solvent (such as N,N-dimethylformamide) and at a convenient temperature (such as 0° C. to 80° C.).

Compounds of general formula (IIa), which may exist in equilibrium with compounds of general formula (IIb), can be prepared by treatment of compounds of general formula (IV), with a base (such as sodium hydride) and a formate ester (such as methyl formate) in a suitable solvent (such as N,N-dimethylformamide) and at a convenient temperature (such as 0° C. to 80° C.).

Alternatively, compounds of general formula (I) can be prepared from acetals of general formula (XIII) by elimination of the elements of the alcohol $R^2OH$ under either acidic or basic conditions, at a suitable temperature and often in a suitable solvent. Examples of reagents or reagent mixtures which can be used for this transformation are lithium di-isopropylamide; potassium hydrogen sulphate (see, for example, T Yamada, H Hagiwara and H Uda, *J. Chem. Soc., Chemical Communications*, 1980, 838, and references therein); and triethylamine, often in the presence of a Lewis acid such as titanium tetrachloride (see, for example, K Nsunda and L Heresi, *J. Chem. Soc., Chemical Communications*, 1985, 1000).

Acetals of general formula (XIII) can be prepared by treatment of alkyl silyl ketene acetals of general formula (XII) with trialkylorthoformates of general formula $(R^2O)_3CH$ in the presence of Lewis acid such as titanium tetrachloride, at a suitable temperature and in a suitable solvent (see, for example, K Saigo, M Osaki and T Mukaiyama, *Chemistry Letters*, 1976, 769).

Alkyl silyl ketene acetals of general formula (XII) can be prepared from esters of general formula (IV) by treatment with a base and a trialkylsilyl halide of general formula $R^3_3SiCl$ or $R^3_3SiBr$, such as trimethylsilyl chloride, or a base and a trialkylsilyl triflate of general formula $R^3_3Si\text{-}OSO_2CF_3$, in a suitable solvent and at a suitable temperature (see, for example, C Ainsworth, F Chen and Y Kuo, *J. Organometallic Chemistry*, 1972, 46, 59).

It is not always necessary to isolate the intermediates (XII) and (XIII); under appropriate conditions, compounds of general formula (I) may be prepared from esters of general formula (IV) in "one pot" by the successive addition of suitable reagents listed above.

Compounds of general formula (IV) wherein Z is optionally substituted amino, oxygen or sulphur, can be prepared from compounds of general formula (V) by treatment with compounds of general formula (VI) in the presence of an acid-binding agent (such as potassium carbonate) in a suitable solvent (such as acetone or N,N-dimethylformamide) and at a convenient temperature.

Alternatively, compounds of general formula (IV) wherein Z is an optionally substituted nitrogen atom, can be prepared from compounds of general formula (V) by reaction with a glyoxylic ester followed by reduction using standard methods as set out in the chemical literature.

Compounds of general formula (IV) wherein Z is a sulphur atom, may also be prepared by treatment of diazonium compounds of general formula (X) with thiolate salts of type (XI). Diazonium compounds of general formula (X) can be prepared by standard procedures as set out in the chemical literature.

Compounds of general formula (V) wherein Z is optionally substituted amino, oxygen or sulphur, can be prepared by standard reactions as set out in the chemical literature.

Compounds of general formula (IV) wherein Z is optionally substituted methylene can be prepared by standard methods as described in the chemical literature. For example, such compounds can be prepared by reduction of cinnamic esters. Alternatively, such compounds can be Prepared from compounds of general formula (VII) by treatment with a salt (such as lithium chloride) in a suitable solvent (such as wet dimethylsulphoxide) and at a convenient temperature (such as 110° C. to 189° C.) (see, for example, A P Krapcho, J F Weimaster, J M Eldridge, E G E Jahngen, Jr, A J Lovey, W P Stephens, J Org Chem, 1978, 43, 138).

Compounds of general formula (VII) wherein Z is optionally substituted methylene can be prepared from compounds of general formula (VIII) wherein Z is optionally substituted methylene by treatment with di-esters of general formula (IX) using standard methods set out in the chemical literature (see, for example, H 0 House, Modern Synthetic Methods, 2nd Edition, p 510).

Compounds of general formula (VIII) wherein Z is optionally substituted methylene, can be prepared by standard reactions as set out in the chemical literature.

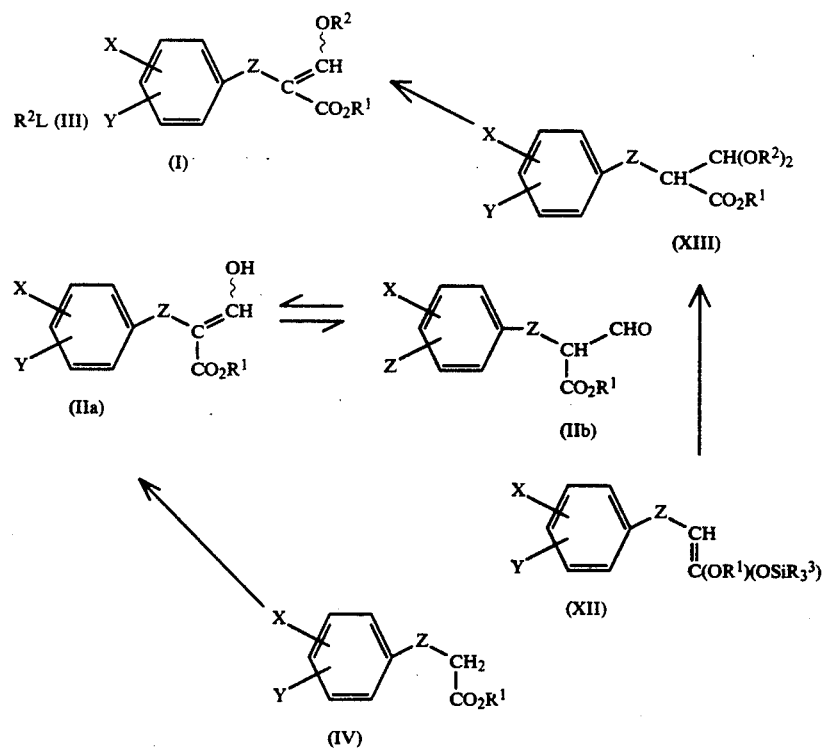

Scheme 1

Scheme 1

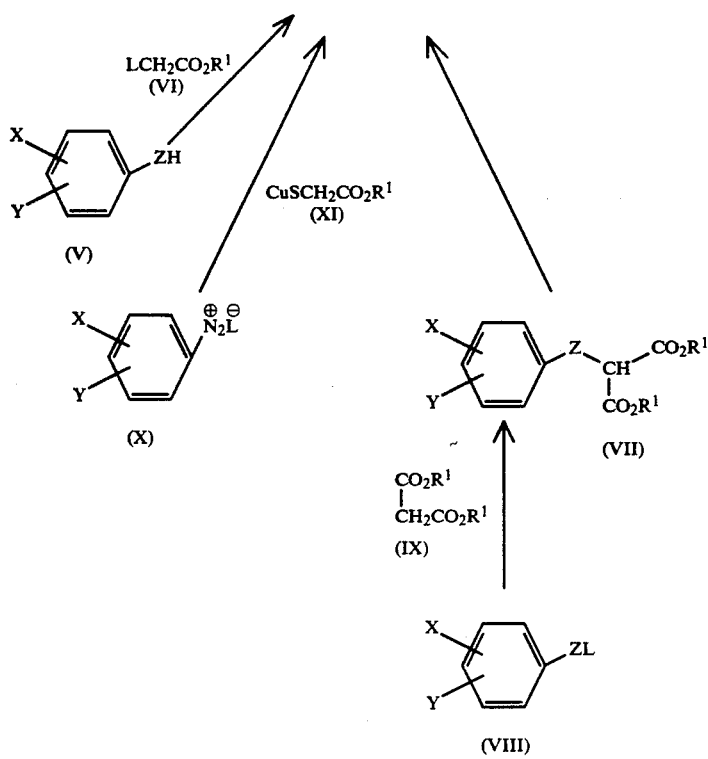

The compounds and metal complexes are active fungicides, particularly against the diseases:

*Pyricularia oryzae* on rice *Puccinia recondita, Puccinia striiformis* and other rusts on wheat, *Puccinia hordei, Puccinia striiformis* and other rusts on barley, and rusts on other hosts eg. coffee, apples, apples, vegetables and ornamental plants *Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines *Helminthosporium* spp., *Rhynchosporium* spp. and *Pseudocercosporella herpotrichoides* on cereals *Cercospora arachidicola* and *Cercosporidium personata* on peanuts and other *Cercospora* species on for example sugar beet, bananas and soya beans and rice. *Botrytis cinerea* (grey mould) on tomatoes, strawberries, vegetables, vines and other hosts *Venturia inaequalis* (scab) on apples and *Plasmopara viticola* (downy mildew) on vines.

Other downy mildews such as *Bremia lactucae* on lettuce, *Peronospora* spp. on soybeans, tobacco, onions and other hosts and *Pseudoperonospora* spp. on hops and curcurbits; *Phytophthora infestans* on potatoes and tomatoes and other *Phytophthora* spp. on vegetables, strawberries, avocado, pepper, ornamentals, tobacco, cocoa and other hosts.

Compounds Nos 5, 10, 14 and 26 of Table I are particularly active fungicides.

The compounds may also be useful as industrial (as opposed to agricultural) fungicides, eg. in the prevention of fungal attack on wood, hides, leather and especially paint films.

The compounds are also useful for the treatment of candidiasis and human dermatophyte infections.

The compounds may be used as such for fungicidal purposes but are more conveniently formulated into compositions for such usage. The invention thus provides a fungicidal composition comprising a compound of general formula (I) as hereinbefore defined, or a metal complex thereof; and, optionally, a carrier or diluent.

Some of the compounds have also shown a broad range of activities against fungi in vitro. They have activity against various post-harvest diseases of fruit (eg. *Penicillium digitatum* and *italicum* and *Trichoderma viride* on oranges and *Gloesporium musarum* on bananas).

The invention also provides a method of combating fungi, which comprises applying to a plant, to seed of a plant, or to the locus of the plant or seed, a compound or metal complex thereof, as hereinbefore defined.

The invention compounds also display plant growth regulating activity.

The plant growth regulating effects of the compounds are manifested as, for example, by a stunting or dwarfing effect on the vegetative growth of woody and herbaceous mono- and di-cotyledonous plants. Such stunting or dwarfing may be useful, for example, in peanuts, cereals such as wheat and barley, oil seed rape, field beans, sunflowers, potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertiliser to be applied. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. The compounds may stunt grasses without significant phytotoxic effects and without deleteriously affecting the appearance (particularly the color) of the grass.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, eg. wheat, barley, rice, maize, soya, sugarbeet, potatoes, plantation crops and orchard crops. By increasing tillering in monocotyledonous crops (eg. rice), the number of flowering shoots per unit area may be increased thereby increasing the overall grain yield of such crops. In addition better control and modification of hierarchical relationships is possible both in vegetative and reproductive stages of monocotyledonous and dicotyledenous plant growth, especially in cereals such as wheat, barley, rice and maize, whereby the number of flowering shoots per unit area may be increased and the size distribution of grains within the ear may be modified in such a way as to increase yield. In grass swards, especially amenity grass, an increase in tillering could lead to a denser sward which may result in increased resilience in wear; and to increased yields and better quality of forage grass, eg. improved digestability and palatability.

The treatment of plants with the compounds can lead to the leaves developing a darker green color. In dicotyledonous plants such as soyabean and cotton, there may be promotion of sideshooting.

Crop yields may also be increased by improvement of the harvest index (ie. the harvested yield as a proportion of the total dry matter produced) by altering dry matter partitioning. This applies particularly to cereal crops.

It is to be understood that not all the compounds of the present invention will necessarily show all the above mentioned plant growth regulating effects. Thus whilst there may be advantages in compounds which have a broad spectrum of plant growth regulating effects against a wide range of species, compounds having a high specific activity with respect to a particular species and/or plant growth regulating effect may also be of great benefit.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. With the use of biodegradable polymeric slow release granules rates of 1 to 10 g per hectare are feasible; whilst electrodynamic spraying techniques may also deploy lower rates of application. However, on certain plants even application rates within these ranges may give undesired phytotoxic effects. Routine tests may be necessary to determine the best rate of application of a specific compound for any specific purpose for which it is suitable.

The compounds may be used as such for plant growth regulating purposes but are more conveniently formulated into compositions for such usage. The invention thus provides a plant growth regulating composition comprising a compound of general formula (I) as hereinbefore defined, or a salt or metal complex thereof; and, optionally, a carrier or diluent.

The invention also provides a method of regulating plant growth, which comprises applying to the plant, to seed of a plant or to the locus of a plant or seed, a compound, or a salt or metal complex thereof, as hereinbefore defined, or a composition combining the same.

The compounds, salts, metal complexes, ethers and esters can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapor; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (eg. 2-ethoxyethanol and 2-butoxyethanol).

The compositions to be used as sprays may also be in the form of aerosols wherein the formulation is held in a container under pressure in the presence of a propellant, eg. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilisers (eg. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants eg. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents ar the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s). These concentrates suitably contain organic acids (eg. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% to 10%, or 0.01% to 10%, by weight of active ingredient(s) may be used.

The compositions of this invention can comprise also one or more additional compound(s) having biological activity, eg. compounds having similar or complementary fungicidal or plant growth activity or compounds having plant growth regulating, herbicidal or insecticidal activity.

The additional fungicidal compound can be, for example, one which is capable of combating ear diseases of cereals (eg. wheat) such as Septoria, Gibberella and Helminthosporium spp., seed and soil borne diseases and downy and powdery mildews on grapes and powdery mildew and scab on apple etc. Examples of suitable additional fungicidal compounds are carbendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl aluminium, fenarimol, iprodione, procymidone, vinclozolin, penconazole, myclobutanil, RO151297, S3308, pyrazophos, ethirimol, ditalimfos, tridemorph, triforine, nuarimol, triazbutyl, guazatine, prop.iconazole, prochloraz, flutriafol, chlortriafol i.e. the chemical 1-(1,2,4-triazol-1-yl) -2-(2,4-dichlorophenyl)-hexan-2-ol, DPX H6573(1-((bis-4-fluorophenyl)methylsilyl)-methyl)-IH-1,2,4-triazole, triadimefon, triadimenol, diclobutrazol, fenpropimorph, fenpropidine, chlorozolinate, diniconazol, imazalil, fenfuram, carboxin, oxycarboxin, methfuroxam, dodemorph, BAS 454, blasticidin S, kasugamycin, edifenphos, kitazin P, cycloheximide, phthalide, probenazole, isoprothiolane, tricyclazole, pyroquilan, chlorbenzthiazone, neoasozin, polyoxin D, validamycin A, reproril, flutolanil, pencycuron, diclomezine, phenazin oxide, nickel dimethyldithiocarba-mate, techlofthalam, bitertanol, bupirimate, etaconazole, streptomycin, cypofuram, biloxazol, quinomethionate, dimethirimol, 1-(2-cyano-2-methoxyimino-acetyl) -3-ethyl urea, fenapanil, tolclofosmethyl, pyroxyfur, polyram, maneb, mancozeb, captafol, chlorothalonil, anilazine, thiram, captan, folpet, zineb, propineb, sulphur, dinocap, binapactryl, nitrothalisopropyl, dodine, dithianon, fentin hydroxide, fentin acetate, tecnazene, quintozene, dichloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophos, buprofezin, ethroproxyfen and cycloprothrin.

Plant growth regulating compounds for use in the invention compositions are compounds which control weeds or seedhead formation, or selectively control the growth of less desirable plants (e.g. grasses).

Examples of suitable plant growth regulating compounds for use with the invention compositions are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluoroecol), maleic hydrazide, glyphosate, glyphosine, long chain fatty alcohols and acids, dikegulac, paclobutrazol, flurprimidol, fluoridamid, mefluidide, substituted quaternary ammonium and phosphonium compounds (e.g. chloromequat chlorphonium or mepiquatchloride), ethephon, carbetamide, methyl-3,6-dichloroanisate, daminozide, asulam, abscisic acid, isopyrimil, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, fenpentezol, inabenfide, triapenthenol and tecnazene.

The following examples illustrate the invention.

Unless otherwise stated, solutions were dried over magnesium sulphate, and chromatography was performed on silica gel. All experiments involving air- or water-sensitive intermediates were conducted under an atmosphere of dry nitrogen.

The following abbreviations are used throughout
Ether = Diethyl ether
THF = Tetrahydrofuran
DMF = N,N-dimethylformamide
gc = Gas chromatography
IR = Infrared
mp = Melting point
HPLC = High Performance Liquid Chromatography
NMR = Nuclear Magnetic Resonance

EXAMPLE 1

This Example illustrates the preparation of Z-methyl 3-methoxy-2-(3'-phenylphenoxy)propenoate (compound No 14 of Table 1).

A mixture of 3-phenylphenol (5.00 g), methyl bromoacetate (3.1 ml) and potassium carbonate (8.1 g) in DMF was stirred at room temperature. After five hours, the reaction mixture was diluted with water (100 ml) and then extracted with ether. The combined organic layers were washed with aqueous sodium carbonate followed by brine and then dried, filtered and evaporated to give crude methyl (3-phenylphenoxy)acetate (7.2g) as a pale yellow liquid, $^1$H NMR (CDCl$_3$) delta 3.8 (3H,s), 4.7 (2H,s), 6.8–7.6 (9H,m) ppm.

Methyl (3-phenylphenoxy)acetate (6.0 g) and methyl formate (30.2 ml) were dissolved in DMF and added dropwise with stirring to a suspension of sodium hydride (1.44 g, 50% dispersion in oil) in DMF at 0° C. (ice-bath). After 45 minutes, the ice-bath was removed and the reaction mixture was stirred for 2 hours at room temperature. Aqueous sodium carbonate was then added. The aqueous layer was washed with ether, acidified to pH 4–5 with concentrated hydrochloric acid and then re-extracted with ether. The combined organic layers were washed with brine, (3'-phenylphenoxy)-propenoate as a pale yellow oil (6.05 g, 90% yield).

Methyl 3-hydroxy-2-(3'-phenylphenoxy)propenoate (6.05 g) and dimethyl sulphate (2.18 ml) were stirred at room temperature in DMF in the presence of potassium carbonate (6.30 g). After two hours, aqueous sodium carbonate was added, the resulting solution was extracted with ether and the combined ether layers were washed successively with water and brine, then dried, filtered and evaporated to give the title compound (4.6 g, 72%) as a white solid which was recrystallised from methanol, mp. 111°–113° C.; $^1$H NMR (CDCl$_3$) delta 3.70 (3H,singlet), 3.82 (3H,singlet), 6.9–7.6 (4H,multiplet) and 7.32 (1H,singlet) ppm.

EXAMPLE 2

This Example describes the preparation of E-methyl 2-benzyl-3-methoxypropenoate (compound No 1 of Table 1).

A mixture of methyl 3-phenylpropanoate (6.90 g) and methyl formate (50.5 g) in dry DMF (50 ml) was added dropwise to a stirred suspension of sodium hydride (2.00 g) in dry DMF (50 ml) at a temperature of between 0° and 5° C. (effervescence). After the addition, the mixture was stirred at 0° C. for 0.5 h and at room temperature for 3.5 h then poured into a mixture of ice and sodium carbonate.

The resulting mixture was washed with ether then acidified with concentrated hydrochloric acid and extracted with ether. The ether extracts were washed with water, dried, and concentrated to give methyl 2-benzyl-3-hydroxypropenoate (2.63 g). This was dissolved in dry DMF (20 ml) and potassium carbonate (3.78 g) and dimethyl sulphate (1.64 g) were added successively with stirring. After 1 hour at room temperature, the reaction mixture was poured into water and extracted with ether. The extracts were washed with water, dried, concentrated, and purified by column chromatography using dichloromethane as eluant to give the title compound as a colorless oil (1.71 g, 21% yield from methyl 3-phenylpropanoate).

EXAMPLE 3

This Example describes the preparation of E-methyl 2-(m-phenylbenzyl)-3-methoxypropenoate (compound No. 5 of Table 1).

3-Phenylbenzyl bromide (melting point 54°–56° C.) was prepared by illumination of a solution of 3-phenyltoluene and N-bromosuccinimide in carbon tetrachloride in the presence of azobisisobutyronitrile.

Solutions of dimethyl malonate (1.32 g) in dry methanol (5 ml) and 3-phenylbenzyl bromide (2.47 g) in dry methanol (5 ml, hot solution) were added successively to a stirred solution of sodium methoxide [from sodium (0.23 g) and dry methanol (20 ml)]. The resulting mixture was stirred for 2 hours at room temperature and for 2 hours under reflux, then poured into water and extracted with ether. The extracts were washed with water, dried, concentrated and purified by column chromatography using a 1:1 mixture of dichloromethane and 40°–60° C. petrol as eluant to give dimethyl (m-phenylbenzyl)malonate (1.77 g, 59%) as a yellow oil, IR (film) : 1 755 and 1 740 cm$^{-1}$.

A mixture of dimethyl (m-phenylbenzyl)malonate (1.00 g) and lithium chloride (0.285 g) in water (0.12 ml) and dimethylsulphoxide (8.5 ml) was heated at 165° C. for 3 hours then allowed to cool, poured into water and extracted with ether. The extracts were washed with water, dried, concentrated, and chromatographed using 10% ether in petrol as eluant to give methyl 3-(m-phenylphenyl)propanoate (0.65 g, 81%) as a colourless oil which solidified on standing, melting point 29°–30° C.

Parallel reactions on a larger scale gave a further sample of methyl 3-(m-phenylphenyl)propanoate.

A solution of methyl 3-(m-phenylphenyl)propanoate (3.54 g) in dry THF (20 ml) was added dropwise to a stirred solution of lithium di-isopropylamide [from di-isopropylamine (2.23 g) and n-butyl-lithium (12.7 ml of 1.6 M solution in n-hexane)] in THF (25 ml) at −70° C.

After 0.5 h. at −70° C., trimethylsilyl chloride (4.01 g) was added to the reaction mixture. It was stirred for 5 minutes at −70° C., then allowed to warm to room temperature and the THF was removed under reduced pressure. The residue was triturated with dry ether, filtered, and the filtrate was again concentrated under reduced pressure. This trituration process was repeated, leaving, from the filtrate, an orange oil (5.53 g) whose infrared spectrum showed almost no ester carbonyl absorption and a strong peak at 1 678 cm$^{-1}$. This crude methyl silyl enol ether was used directly for the next step.

A solution of titanium tetrachloride (1.61 ml) in dry dichloromethane (4 ml) was added dropwise to a stirred solution of trimethylorthoformate (1.45 ml) in dry dichloromethane (30 ml) at −70° C. (exothermic). After 15 minutes at this temperature, a solution of the crude methyl silyl enol ether as described above (5.53 g) in dry methane (20 ml) was added dropwise, still at −70° C. (again, exothermic). After a further 30 minutes at the same temperature, 5% aqueous potassium carbonate was added and the mixture was extracted with ether. The extracts were washed with water, dried, concentrated under reduced pressure, and chromatographed using 40% ether in petrol as eluant to give methyl 3,3-dimethoxy-2-(m-phenylbenzyl)propanoate [2.79 g, 60% yield from methyl 3-(m-phenylphenyl)propanoate] as a pale yellow oil, IR (film): 1 735 cm$^{-1}$.

A solution of methyl 3,3-dimethoxy-2-(m-phenylbenzyl)propanoate (2.50 g) in dry THF (15 ml) was added dropwise to a stirred solution of lithium di-isopropylamide [from n-butyl-lithium (5.9 ml of a 1.6 M solution in n-hexane) and di-isopropylamine (1.12 g)] in dry THF (15 ml) at −78° C. The mixture was stirred at this temperature for 30 minutes, then poured into water and extracted with ether. The extracts were washed with water, dried, concentrated under reduced pressure, and purified by chromatography using dichloromethane as eluant to give the title compound (1.44 g, 64%) as a pale yellow oil, IR (film): 1 710, 1 660 cm$^{-1}$.

EXAMPLE 4

This Example describes the preparation of Z-methyl 3-methoxy-2-(3'-phenylthiophenoxy)propenoate (Compound No. 26 of Table 1).

To 3-phenylaniline (8.02 g) was added sulphuric acid (40 ml, 10%). The resultant white suspension was cooled to 0° C. and then treated dropwise with a solution of sodium nitrite (3.35 g) in water (20 ml). The copper salt of methyl thioglycolate (formed as a yellow precipitate by treating an aqueous solution of copper sulphate with methyl thioglycolate) was then added portionwise with stirring. The solution became a tan color and nitrogen was evolved. The solution was then transferred to a 2l beaker, stirred until room temperature was reached and then extracted with diethyl ether (3×150 ml). The combined organic layers were washed successively with 10% hydrochloric acid (3×100 ml), 10% aqueous sodium hydroxide solution (3×10 ml) and water, and then dried. Evaporation of the solvent yielded 6.98 g of crude product which was separated on silica gel (eluent ethanol) to give methyl (3-phenylthiophenoxy)acetate (6.60 g).

Methyl (3-phenylthiophenoxy)acetate (6.60 g) and methyl formate (30.78 g) were dissolved in DMF (30 ml) and added dropwise at 0° C. to sodium hydride (0.83 g, 50% dispersion in oil) in DMF. The reaction mixture was stirred at 0° C. for 45 minutes and then left at room temperature under nitrogen over the weekend. The reaction mixture was then poured into water (300 ml) and washed with diethyl ether (3×150 ml). The aqueous phase was adjusted to pH 7 with hydrochloric acid and then extracted with diethyl ether (3×100 ml). The combined organic extracts were washed successively with water (3×100 ml) and brine (2×75 ml) and then dried. Filtration and evaporation of the solvent under reduced pressure gave methyl 3-hydroxy-2-(3'-phenylthiophenoxy)propenoate (1.13 g) which was used without further purification.

Methyl 3-hydroxy-2-(3'-phenylthiophenoxy)propenoate (1.13 g) was treated with dimethyl sulphate (0.63 g) and potassium carbonate (1.17 g) in DMF (35 ml). The reaction mixture was worked up as before to give 0.91 g of crude product. HPLC (eluent dichloromethane) on silica gel afforded the title compound (440 mg) as an oil, m/e 300 (M+), 268, 197, 75.

EXAMPLE 5

This Example describes the preparation of Z-methyl 3-methoxy-2-(N-methyl-3'-phenylanilino)propenoate (Compound No. 10 of Table 1).

3-Phenylaniline (7.80 g) was stirred in dry methanol (100 ml) with methyl glyoxalate (4.10 g) for 1 hour over 3 angstrom molecular sieves. A solution of sodium cyanoborohydride (1.48 g) in dry methanol was then added dropwise and the resulting mixture was stirred overnight. The reaction mixture was filtered and the filtrate was concentrated under reduced pressure. The residue was dissolved in ether and then extracted with 2M hydrochloric acid. The aqueous extracts were neutralized with sodium carbonate and then extracted with ether. Evaporation of these ether extracts yielded crude methyl (3-phenylanilino)acetate (5.76 g) as a brown oil. The reaction was repeated on a larger scale (8.11 g) to afford 8.78 g product as a yellow oil. Treatment of the product (5.50 g) for 5 hours with methyl iodide (8.20 g) and potassium carbonate (6.83 g) in DMF (50 ml) gave methyl (N-methyl-3-phenylanilino)acetate (4.33 g) as a brown oil ($^1$H NMR (CDCl$_3$) delta 3.10 (3H,s); 3.70 (3H,s); 4.10 (2H,s) ppm; IR 1730 cm$^{-1}$; 92% pure by gc) which was used without further purification.

Methyl (N-methyl-3-phenylanilino)acetate (4.33 g) was formylated as described in Example 1 by treatment with sodium hydride (0.94 g) and methyl formate (21.01 g) in DMF (50 ml) to give methyl 3-hydroxy-2-(N-methyl-3'-phenylanilino)propenoate (0.60 g) as a brown viscous liquid. Methylation with dimethyl sulphate (0.59 g) and potassium carbonate (0.62 g) in DMF (25 ml) for 5 hours afforded on work-up and HpLC (eluent petroleum ether—ether, 70:30) on silica gel a pure sample of the title compound (260 mg) as a yellow liquid.

EXAMPLE 6

An emulsifiable concentrate was made up by mixing the ingredients, and stirring the mixture until all the constituents were dissolved.

| | |
|---|---|
| Compound 14 of Table 1 | 10% |
| Ethylene dichloride | 40% |
| Calcium dodecylbenzenesulphate | 5% |
| "Lubrol" L | 10% |
| "Aromasol" H | 35% |

EXAMPLE 7

A composition in the form of grains readily dispersible in a liquid, eg. water, was prepared by grinding together the first three ingredients in the presence of added water and then mixing in the sodium acetate. The resultant mixture was dried and passed through a British Standard mesh sieve, size 44-100, to obtain the desired size of grains.

| | |
|---|---|
| Compound 14 of Table 1 | 50% |
| "Dispersol" T | 25% |
| "Lubrol" APN5 | 1.5% |
| Sodium acetate | 23.5% |

EXAMPLE 8

The ingredients were all ground together to produce a powder formulation readily dispersible in liquids.

| | |
|---|---|
| Compound 14 of Table 1 | 45% |
| "Dispersol" T | 5% |
| "Lissapol" NX | 0.5% |
| "Cellofas" B600 | 2% |
| Sodium acetate | 47.5% |

EXAMPLE 9

The active ingredient was dissolved in a solvent and the resultant liquid was sprayed on to the granules of China clay. The solvent was then allowed to evaporate to produce a granular composition.

| | |
|---|---|
| Compound 14 of Table 1 | 5% |
| China clay granules | 95% |

EXAMPLE 10

A composition suitable for use as a seed dressing was prepared by mixing the three ingredients.

| | |
|---|---|
| Compound 14 of Table 1 | 50% |
| Mineral oil | 2% |
| China clay | 48% |

EXAMPLE 11

A dusting powder was prepared by mixing the active ingredient with talc.

| | |
|---|---|
| Compound 14 of Table 1 | 5% |
| Talc | 95% |

EXAMPLE 12

A Col formulation was prepared by ball-milling the constituents set out below and then forming an aqueous suspension of the ground mixture with water.

| | |
|---|---|
| Compound 14 of Table 1 | 40% |
| "Dispersol" T | 10% |
| "Lubrol" APN5 | 1% |
| Water | |

EXAMPLE 13

A dispersible powder formulation was made by mixing together the ingredients set out below and then grinding the mixture until all were thoroughly mixed.

| | |
|---|---|
| Compound 14 of Table 1 | 25% |
| "Aerosol" OT/B | 2% |
| "Dispersol" A.C. | 5% |
| China clay | 28% |
| Silica | 40% |

EXAMPLE 14

This Example illustrates the preparation of a dispersible powder formulation. The ingredients were mixed and the mixture then ground in a comminution mill.

| | |
|---|---|
| Compound 14 of Table 1 | 25% |
| "Perminal" BX | 1% |
| "Dispersol" T | 5% |
| Polyvinylpyrrolidone | 10% |
| Silica | 25% |
| China clay | 34% |

EXAMPLE 15

The ingredients set out below were formulated into a dispersible powder by mixing then grinding the ingredients.

| | |
|---|---|
| Compound 14 of Table 1 | 25% |
| "Aerosol" OT/B | 2% |
| "Dispersol" A | 5% |
| China clay | 68% |

In Examples 6 to 15 the proportions of the ingredients given are by weight.

The compounds set out in Tables 1 and 2 are similarly formulated as specifically described in Examples 6 to 15.

There now follows an explanation of the compositions or substances represented by the various Trade Marks and Trade Names mentioned above.

| | |
|---|---|
| LUBROL L: | a condensate of nonyl phenol (1 mole) with ethylene oxide (13 moles) |
| AROMASOL H: | a solvent mixture of alkylbenzenes |
| DISPERSOL T & AC: | a mixture of sodium sulphate and a condensate of formaldehyde with sodium naphthalene sulphonate |
| LUBROL APN5: | a condensate of nonyl phenol (1 mole) with naphthalene oxide (5.5 moles) |
| CELLOFAS B600: | a sodium carboxymethyl cellulose thickener |
| LISSAPOL NX: | a condensate of nonyl phenol (1 mole) with ethylene oxide (8 moles) |
| AEROSOL OT/B: | dioctyl sodium sulphosuccinate |
| PERMINAL BX: | a sodium alkyl naphthalene sulphonate |

EXAMPLE 16

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed on to the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4 = no disease
3 = trace—5% of disease on untreated plants
2 = 6-25% of disease on untreated plants
1 = 26-59% of disease on untreated plants
0 = 60-100% of disease on untreated plants The results are shown in Table 4.

TABLE 4

| COMPOUND NUMBER | PUCCINIA RECONDITA (WHEAT) | ERYSIPHE GRAMINIS (BARLEY) | VENTURIA INAEQUALIS (APPLE) | PYRICULARIA ORYZAE (RICE) |
| --- | --- | --- | --- | --- |
| 4 | 1 | 0 | 3 | 0 |
| 5 | 4 | 3 | 4 | 0 |
| 6 | 0 | 0 | 0 | 2 |
| 7 | 0 | 0 | 2 | 0 |
| 8 | 0 | 4 | 4 | 4 |
| 10 | 4 | 4 | 1 | 3 |
| 11 | 0 | 0 | 0 | 0 |
| 12 | 0 | 0 | 2 | 0 |
| 13 | 0 | 0 | 2 | 0 |
| 14 | 4 | 0 | 4 | 3 |
| 16 | 3 | 1 | 0 | 0 |
| 19 | 2 | 0 | 0 | 0 |
| 20 | 3 | 0 | 0 | 0 |
| 23 | 0 | 0 | 0 | 0 |
| 24 | 0 | 0 | 0 | 3 |
| 26 | 4 | 4 | 4 | 2 |
| 138 | — | 2 | — | 4 |

| COMPOUND NUMBER | CERCOSPORA ARACHIDICOLA (PEANUT) | PLASMOPARA VITICOLA (VINE) | PHYTOPHTHORA INFESTANS (TOMATO) |
| --- | --- | --- | --- |
| 4 | 0 | 0 | 0 |
| 5 | 3 | 4 | — |
| 6 | 0 | 0 | — |
| 7 | — | 0 | — |
| 8 | 1 | 4 | — |
| 10 | 4 | 4 | 4 |
| 11 | 0 | 2 | — |
| 12 | 0 | 0 | — |
| 13 | 0 | 0 | — |
| 14 | 3 | 4 | — |
| 16 | 0 | 4 | — |
| 19 | 0 | 0 | — |
| 20 | 2 | 0 | — |
| 23 | 1 | 0 | — |
| 24 | 0 | 3 | — |
| 26 | 4 | 4 | — |
| 138 | — | 3 | 0 |

EXAMPLE 17

Whole Plant Screen (2)

Compounds numbers 1-3, 6-8, 12-19, 21, 23-24 were tested on an alternative whole plant screen (2). The compounds were tested for plant growth regulator activity against five species for various growth effects relevant to plant growth regulation.

Methodology

The plant species used in this screen are presented in Table 5 with the leaf stage at which they were sprayed. Each chemical was applied at 4000 ppm (4 kg/ha in a 1000 l/ha field volume) apart from compound No. 2 which was applied at 1000 ppm (1 kg/ha in a 1000 l/ha field volume) using a tracksprayer and a SS8004E (Teejet) nozzle.

After spray the plants were grown in a glasshouse with 25° C. day/22° C. night temperatures and supplementary lighting was supplied when necessary (from mercury vapor lamps), to provide a 16 hour photoperiod. The exceptions to this were the temperature cereals, wheat and barley which were grown in 16° C. day/13° C. night temperatures.

After 2-6 weeks in the glasshouse, depending on the time of year, the plants were visually assessed for morphological characteristics. Formulation blanks were used as controls to assess the plants. The results are presented in Table 6.

TABLE 5
PLANT MATERIAL USED FOR WHOLE PLANT SCREEN(2)

| Species | Code | Variety | Growth Stage at Treatment | No. Plants per 3" Pot | Compost Type |
|---|---|---|---|---|---|
| Barley | BR | Atem | 1–1.5 leaves | 4 | JIP* |
| Wheat | WW | Timmo | 1–1.5 leaves | 4 | JIP |
| Maize | MZ | Earliking | 2¼ leaves | 1 | PEAT |
| Apple | AP | Red Delicious | 4–5 leaves | 1 | JIP |
| Rice | RC | Ishikari | 2–2½ leaves | 4 | JIP |

JIP* = John Innes Potting Compost.

TABLE 6

| SPECIES | COMPOUND NO. | R | G | A | T | I |
|---|---|---|---|---|---|---|
| WW | 1 | | 2 | 2 | 3 | 3 |
| | 7 | 1 | | | 1 | |
| | 23 | | | | 1 | |
| BR | 15 | | | | 1 | |
| | 18 | 1 | | | | 2 |
| | 23 | 1 | | | | 1 |
| MZ | 1 | | | 1 | | |
| | 3 | | | | 1 | 1 |
| | 7 | | | | 1 | |
| | 8 | 1 | | 1 | | 1 |
| | 12 | | | | 1 | |
| | 16 | 2 | 2 | 3 | | 2 |
| | 19 | 2 | 2 | 2 | | 1 |
| | 21 | 1 | | 1 | | |
| | 23 | 2 | 2 | 2 | | 2 |
| | 24 | 1 | 1 | 2 | | 1 |
| RC | 2 | | | | 1 | |
| | 6 | 2 | | | | 2 |
| | 14 | | | | 1 | |
| | 24 | 2 | | | | 1 |
| AP | 18 | 1 | | | | 1 |

Key:
R = Retardation
G = Greening effect
A = Apical damage
T = Tillering or side shooting
I = Interligular or internodal length reduction
All effects are scored visually on a 1-3 basis where
1 = 10–30%
2 = 31–60%
3 = 61–100%
Blank means less than 10% effect.

We claim:

1. A compound having the formula (I):

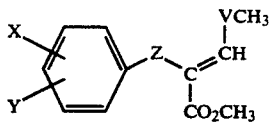

and stereoisomers thereof, wherein V is oxygen or sulphur; X is hydrogen, $C_{1-4}$ alkyl, $C_{3-4}$ alkenyl, halogen, phenyl, naphthyl, benzyl, phenoxy or benzyloxy, each aryl moiety being optionally substituted with one or more of halogen, $C_{1-4}$ alkyl, $C_{1-4}$ alkoxy or halo($C_{1-4}$)alkyl; Y is hydrogen or halogen, provided that X and Y are not both hydrogen or X and Y together, when they are in adjacent positions on the phenyl ring, form a fused benzene ring; and Z is $CH_2$, $CH(CH_3)$ or $C(CH_3)_2$.

2. A compound as claimed in claim 1 wherein X is attached to the phenyl ring at the meta- (or 3-) position relative to the group Z, and X is a phenyl or naphthyl, group each linked through any one of their ring atoms and each optionally substituted with one or more halogen atoms or $C_{1-4}$ alkyl, $C_{1-4}$ alkoxy or halo ($C_{1-4}$) alkyl groups.

3. A compound as claimed in claim 1 wherein X is $C_{1-4}$ alkyl, phenyl, naphthyl, phenoxy or benzyloxy each aryl moiety being optionally substituted with one or more of halogen, $C_{1-4}$ alkyl, $C_{1-4}$ alkoxy or trifluoromethyl; and Y is hydrogen or halogen; or X and Y together, when they are in adjacent positions on the phenyl ring, form a fused benzene ring.

4. A compound as claimed in claim 1 of formula:

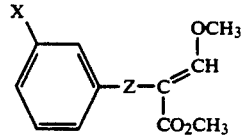

wherein X is phenyl, or phenoxy, each optionally substituted with one or more of halogen, $C_{1-4}$ alkyl, $C_{1-4}$ alkoxy or trifluoromethyl.

5. A compound according to claim 1 wherein X is meta to the linking group Z and is phenyl, naphthyl, benzyl, phenoxy or benzyloxy, each optionally substituted with halogen, $C_{1-4}$ alkyl, $C_{1-4}$ alkoxy or halo ($C_{1-4}$)alkyl.

6. A fungicidal composition comprising, as an active ingredient, a compound as claimed in claim 1 together with a carrier therefor.

7. A method of combating fungi, which comprises applying to a plant, to a seed of a plant, or to the locus of the plant or seed, a compound having the formula:

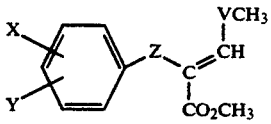

and stereoisomers thereof, wherein V is oxygen or sulphur; X is hydrogen, $C_{1-4}$ alkyl, $C_{3-4}$ alkenyl, halogen, phenyl, naphthyl, benzyl, phenoxy or benzyloxy, each aryl moiety being optionally substituted with one or more of halogen, $C_{1-4}$ alkyl, $C_{1-4}$ alkoxy or halo($C_{1-4}$)alkyl; Y is hydrogen or halogen, or X and Y together, when they are in adjacent positions on the phenyl ring, form a fused benzene ring; and Z is $CH_2$, $CH(CH_3)$ or $C(CH_3)_2$.

* * * * *